United States Patent [19]

Brown et al.

[11] Patent Number: 5,516,905
[45] Date of Patent: May 14, 1996

[54] ANTIBIOTIC COMPOUNDS AND METHODS TO TREAT GRAM-POSITIVE BACTERIAL AND MYCOPLASMAL INFECTIONS

[75] Inventors: Neal C. Brown, Northboro; George Wright, Worcester, both of Mass.

[73] Assignee: University of Massachusetts Medical Center, Worcester, Mass.

[21] Appl. No.: 298,011

[22] Filed: Aug. 30, 1994

[51] Int. Cl.$^6$ .............. C07D 239/02; C07D 473/00; A61K 31/505

[52] U.S. Cl. .............. 544/312; 544/276; 544/277; 544/321

[58] Field of Search .............. 544/312, 321; 514/269, 272

[56] References Cited

PUBLICATIONS

Boxer et al., "Structural and Enzymological Characterization of the Homogeneous Deoxyribonucleic Acid Polymerase from *Mycoplasma orale*", Biochemistry 18:4742–4749, (1979).

Barnes et al., "Antibody to B. subtilis DNA polymerase III: use in enzyme purification and examination of homology among replication–specific DNA polymerases", Nucleic Acids Research, 6(3):1203–1219, (1979).

Barnes et al., "Localization of the exonuclease and polymerase domains of *Bacillus subtilis* DNA polymerase III", Gene, 111:43–49, (1992).

Bazill et al., "Effect of 6–(P–Hydroxyphenyl)–azouracil on B. subtilis DNA Polymerases", Nature New Biology, 240:82–83, (1972).

Brown et al., "Inhibitors of *Bacillus subtilis* DNA Polymerase III. 6–(Arylalkylamino)uracils and 6–Anilinouracils", Journal of Midicinal Chemistry, 20:1186–1189, (1977).

Brown et al., "Rational Design of Substrate Analogues Targeted to Selectively Inhibit Replication–Specific DNA Polymerases", Drugs Under Experimental and Clinical Research, 12(6/7):555–564, (1986).

Brown, "6–(p–Hydroxyphenylazo)–uracil: A Selective Inhibitor of Host DNA Replication in Phage–Infected *Bacillus subtilis*", Proceedings of the National Acadamy of Sciences, 67(3):1454–1461, (1970).

Butler, "Development of novel inhibitor probes of DNA polymerase III based on dGTP analogs of the HPUra type: base, nucleoside and nucleotide derivatives of $N^2$–(3, 4–dichlorobenzyl)guanine", Nucleic Acids Research, 18(24):7381–7387, 1990.

Hammond et al., "*Bacillus subtilis* DNA polymerase III: complete sequence, overexpression, and characterization of the polC gene", Gene, 98:29–36, (1991).

Low et al., "Purification and Characterization of DNA Polymerase III from *Bacillus subtilis*", The Journal of Biological Chemistry, 251(5):1311–1324, (1976).

Maurel et al., "Mollicutes DNA Polymerases: Characterization of a Single Enzyme from Mycoplasma Mycoides and Ureaplasma Urealyticum and of three enzymes from Acoleplasma Laidlaw II", Res. Microbiol., 140:191–205 (1989).

Mills et al., "Purification and Partial Characterization of the Principal Deoxyribonucleic Acid Polymerase from Mycoplasmatales", Journal of Bacteriology, 132(2):641–649, (1977).

Neville et al., "Inhibition of a Discrete Bacterial DNA Polymerase by 6–(p–Hydroxy–phenylazo)–uracil and 6–(p–Hydroxy–phenylazo–)–isocytosine", Nature New Biology, 240(96):80–82, (1972).

Nogimori et al., "Synthesis of 6–Anilino–2–thiouracils and Their Inhibition of Human Placenta Iodothyronine Deiodinase", Journal of Medicinal Chemistry, 23(11):1692–1694, (1985).

Razin, "Peculiar properties of mycoplasmas: The smallest self–replicating prokaryotes", FEMS Microbiology Letters, 100:423–432, (1992).

Roberts, Mycoplasmas Molecular Biology and Pathogenesis, Chapter 31. Antibiotic Resistance, Jack Maniloff Editor, 513–523 (1991).

Trantolo et al., "Inhibitors of *Bacillus subtilis* DNA Polymerase III. Influence of Modifications in the Pyrimidine Ring of Anilino– and (Benzylamino)pyrimidines", Journal of Medicinal Chemistry, 29(5):676–681, (1986).

Woese, "Bacterial Evolution", Microbiological Reviews, J. L. Engraham, Editor, 51(2):221–271, (1987).

Wright et al., "Deoxyribonucleotide Analogs as Inhibitors and Substrates of DNA Polymerases", Pharmacology & Therapeutics, 47(3):447–497, (1990).

Wright et al., "Synthesis of 6–(Phenylhybrazino)uracils and Their Inhibition of a Replication–Specific Deoxyribonucleic Acid Polymerase", Journal of Medicinal Chemistry, 17:1277–1282, (1974).

*Primary Examiner*—Cecilia Tsang
*Attorney, Agent, or Firm*—Fish & Richardson

[57] ABSTRACT

A method of inhibiting replication of mycoplasmal and Gram-positive bacteria is described. Useful new compounds for in vivo and in vitro inhibition and therapy for infections utilize HPUra-like compounds are also provided. These include a number of novel 3-substituted uracil and isocytosine compounds, and 10-substituted guanine and adenine compounds.

12 Claims, 1 Drawing Sheet

FIG. 1

ANTIBIOTIC COMPOUNDS AND METHODS TO TREAT GRAM-POSITIVE BACTERIAL AND MYCOPLASMAL INFECTIONS

STATEMENT AS TO FEDERALLY SPONSORED RESEARCH

This work was supported in part by the United States government, National Institute of Health Grants GM21747 and GM45330. The government may have certain rights in the invention.

BACKGROUND OF THE INVENTION

The invention relates to mycoplasma and Gram positive bacterial infections.

Gram-positive eubacteria contain three distinct DNA polymerase-exonucleases ("pol-exos"): Pol I, Pol II, and Pol III. Gram-positive Pol III is an enzyme which is absolutely required for the replicarive synthesis of DNA that accompanies the cyclical duplication of the host chromosome. The Gram-positive Pol IIIs are the exclusive targets of the Gram-positive-selective 'HPUra' (6-(p-Hydroxyphenylazo)-uracil) class of antimicrobial agents, i.e., HPUra-like compounds. These agents exert their action by mimicking purine deoxyribonucleotide-triphosphates and physically inhibiting the DNA polymerases.

All known mycoplasmata are parasites of humans, vertebrates, plants, and arthropods. Species known or suspected to be human pathogens include *M. pneumoniae, M. genitalium, M. penetrans*, and, in AIDS patients especially, *M. fermentans*, strain incognitus. Mycoplasma infections in humans and animals are generally of a chronic nature and host immune reactions appear to play a major role in the pathogenesis of such infections. Especially problematic are autoimmunogenic responses elicited by mycoplasmal infections (e.g., rheumatoid-like arthritis, central nervous system symptoms and other types of organ dysfunction).

Mycoplasmata are the smallest and simplest prokaryotes capable of self-replication. They have arisen from conventional Gram-positive bacteria via rapid, degenerative evolution, apparently resulting in significant simplification of the typical Gram-positive genome. A mycoplasmal genome may be as small as 600 kb (but may be as large as 1700 kb) and carry fewer than 500 genes (about one fifth the number of genes as in *E. coli*). This simplified existence is made possible by parasitism.

It is thought that the genome reduction of mycoplasmata has affected the DNA polymerase family of enzymes, reducing the three exo-positive enzymes found in Gram-positive bacteria to a single exo-deficient species (Boxer et al., *Biochemistry*, 18:4742–49 (1979); Maurel et al., *Res. Microbiol.*, 140:191–205 (1989); Mills et al., *J. Bacteriol.*, 132:641–49 (1977)).

Previous investigations have identified only a single DNA polymerase in Mycoplasma. The enzyme from Mycoplasma orale has been purified and found to consist of a single peptide of 103–116 kDa, and a polymerase of the same size has been found in *Mycoplasma hyorhinis*. A 98 kDa polymerase also has been found in *Mycoplasma mycoides*. In contrast to the prototypic Gram-positive- and Gram-negative-specific pols I and II, both of which integrate the activity of at least one exo (3'-5' and/or 5'-3'), none of the previously described mycoplasmal enzymes is exo-positive.

SUMMARY OF THE INVENTION

We have identified compounds which inhibit Gram-positive bacterial and Mycoplasma DNA polymerase III and thus inhibit the growth of bacteria and mycoplasmata. New compounds are provided for use in the inhibition of both mycoplasma and Gram-positive bacteria. In addition, we provide methods for using both the new compounds and some previously known compounds for the inhibition of mycoplasma and Gram-positive bacterial cells.

Accordingly, the invention features a method to inhibit the replication of mycoplasmal cells in vivo and in vitro. This method involves administering, in an amount sufficient to be effective for inhibition, compounds of the invention or any other "HPUra-like" deoxyribonucleotide analog which inhibits the activity of the enzyme DNA polymerase III (e.g., pyrimidine or purine derivatives, 2-substituted dATP and $N^2$-substituted dGTP analogs, ribo-, 2'-deoxyribo-, arabino-, 2',3'-dideoxy- or acyclo-nucleotides, $N^6$-substituted 6-aminopyrimidines and $N^2$-substituted 2-aminopurines) to contact the cells.

By "inhibiting" is meant reducing the cellular growth rate by at least 80%, more preferably 90%, even more preferably 95% and, most preferably by 99% or more. The degree of inhibition may be ascertained by an in vitro growth assay (e.g., by standard liquid culture techniques, the relative number of other colony forming units on an again MIC platae (supra) or dose-response experiments). Compounds showing inhibition of colony formation at a suitable (minimal inhibitory concentration) LD50 will be useful for further examination as therapeutic agents.

By "effective amount" of a compound is meant an amount which, when administered in vivo or in vitro, will achieve the above-stated levels of inhibition.

Another featured aspect is a method to inhibit growth of Gram-positive bacteria in vivo or in vitro by administering, in an amount sufficient to be effective for inhibition, compounds of the invention which have the following general formulae:

wherein $R_1$ is $(CH_2)_nOH$, $CH_2CHOHCH_2OH$, $CH_2CHOHCH_3$, $(CH_2)_mCO_2H$, or $(CH_2)_nNH_2$, n is 2, 3, 4, or 5 and m is 1, 2, 3, or 4; and $R_2$ is where $R_3$ and $R_4$ are H, alkyl, halo, or any other hydrophobic constituents.

In preferred embodiments of both methods, the treatment is administered to an animal (e.g., swine, chicken, or other commercially relevant livestock) or to a human patient which has been diagnosed with a mycoplasmal or Gram-positive bacterial infection. In preferred embodiments, the compounds may be administered to the animal or human to prevent a mycoplasmal or Gram-positive bacterial infection, particularly in an animal or human which is susceptible to such infections (e.g., a human patient with AIDS or one who has recently undergone a medical procedure. In other preferred embodiments, the treatment is administered to cultured eukaryotic cells, either those that have a mycoplasmal or Gram positive bacterial infection, or to prevent such an infection (e.g., prophylactic treatment). Culture medium may be prepared commercially to contain compounds of the invention.

In preferred embodiments, the compounds used in the methods are one or more of the following compounds:
A) 3-(2-Hydroxyethyl)-6-(5-indanylamino)uracil, HE-TMAU ("TMA" indicates 5-indanylamino, also referred to as 3,4 -trimethylenea nilino);
B) 3-(2-Hydroxyethyl)-6-(5 -indanylamino)isocytosine, HE-TMAiC;
C) 3-(2-Hydroxyethyl)-6-(3-ethyl-4-methylanilino)uracil, HE-EMAU;
D) 3-(2-Hydroxyethyl)-6-(3-ethyl-4-methylanilino)isocytosine, HE-EMAiC;
E) 3-(2-Hydroxyethyl)-6-(3,4-dichlorobenzylamino)uracil, HE-DCAU;
F) 3-(2-Hydroxyethyl) - 6-(3,4-dichlorobenzylamino)isocytosine, HE-DCAiC;
G) 3-(4-Hydroxybutyl)-6-(5-indanylamino)uracil, HB-TMAU;
H) 3-(4-Hydroxybutyl)-6-(5-indanylamino)isocytosine, HB-TMAiC;
I) 3-(Carboxymethyl)-6-(5-indanylamino)uracil, CM-TMAU;
J) 3-(2-Aminoethyl)-6-(5-indanylamino)uracil, AE-TMAU;
K) 9-(2- Hydroxyethyl)- $N^2$-(5-indanyl)guanine, HE-TMPG;
L) 9-(2-Hydroxyethyl)-2-(5-indanylamino)adenine, HE-TMAA;
M) 9-(2-Hydroxyethyl)-$N^2$-(3-ethyl-4-methylphenyl)guanine, HE-EMPG;
N) 9-(2-Hydroxyethyl)-2-(3-ethyl-4-methylanilino)adenine, HE-EMAA;
O) 9-(2-Hydroxyethyl)-$N^2$-(3,4-dichlorobenzyl)guanine, HE-DCBG;
P) 9-(2-Hydroxyethyl)-2-(3,4-dichlorobenzylamino)adenine, HE-DCBA;
Q) 9-(4-Hydroxybutyl)-$N^2$-(3,4-dichlorobenzyl)guanine, HB-DCBG;
R) 9-(4-Hydroxybutyl)-2-(3,4-dichlorobenzylamino)adenine, HB-DCBA;
S) 9-(2-Carboxyethyl)-N2-(3,4-dichlorobenzyl)guanine, CE-DCBG; and
T) 9-(2-Aminoethyl)-N2-(3,4-dichlorobenzyl) guanine, AE-DCBG.

The invention also features 3-substituted uracil and isocytosine compounds or their pharmaceutically acceptable salts having the general formulae:

Uracils Isocytosines where $R_1$ in both uracils and isocytosines is $(CH_2)_nOH$, $CH_2CHOHCH_2OH$, $CH_2CHOHCH_3$, $(CH_2)_mCO_2H$, or $(CH_2)_nNH_2$, n is 2, 3 4, or 5 and m is 1, 2, 3, or 4; and $R_2$ is where $R_3$ and $R_4$ are H, alkyl, halo, or any other hydrophobic constituents (e.g., $CH_3$, $C_2H_5$, F, Cl, Br, and $(CH_2)_3$)

Preferred 3-substituted uracil and isocytosine compounds to be used in the invention are:
A) 3-(2-Hydroxyethyl)-6-(5-indanylamino)uracil, HE-TMAU (TMA indicates to 5-indanylamino or 3,4-trimethyleneanilino);
B) 3-(2- Hydroxyethyl)-6-(5-indanylamino)isocytosine, HE-TMAiC;
C) 3-(2-Hydroxyethyl)-6-(3-ethyl-4-methylanilino)uracil, HE- EMAU;
D) 3-(2-Hydroxyethyl)-6-(3-ethyl-4-methylanilino)isocytosine, HE-EMAiC;
E) 3-(2-Hydroxyethyl)-6-(3,4-dichlorobenzylamino)uracil, HE-DCAU;
F) 3-(2-Hydroxyethyl)-6-(3,4-dichlorobenzylamino)isocytosine, HE-DCAiC;
G) 3-(4-Hydroxybutyl)-6-(5-indanylamino)uracil, HB-TMAU;
H) 3-(4-Hydroxybutyl)-6-(5-indanylamino)isocytosine, HB-TMAiC;
I) 3-(Carboxymethyl)-6-(5-indanylamino)uracil, CM-TMAU; and
J) 3-(Aminoethyl)6-(5-indanylamino)uracil, AE-TMAU Another aspect of the invention features 9-substituted guanine and adenine compounds of the general formulae:

Guanines Adenines where $R_1$ in both the guanine and adenine compounds is $(CH_2)_nOH$, $CH_2CHOHCH_2OH$, $CH_2CHOHCH_3$, $(CH_2)_mCO_2H$, or $(CH_2)_nNH_2$, n is 2, 3, 4, or 5 and m is 1, 2, 3, or 4; and $R_2$ is where $R_3$ and $R_4$ are H, alkyl, halo, or any other hydrophobic constituents, e.g., $CH_3$, $C_2H_5$, F, Cl, Br, and $(CH_2)_3$.

Preferred 9-substituted guanine and adenine compounds for use in the invention are:

A) 9-(2-Hydroxyethyl)-$N^2$-(5-indanyl)guanine, HE-TMPG;
B) 9-(2-Hydroxyethyl)-2-(5-indanylamino)adenine, HE-TMAA;
C) 9-(2-Hydroxyethyl)-$N^2$-(3-ethyl-4-methylphenyl)guanine, HE-EMPG;
D) 9-(2-Hydroxyethyl)-2-(3-ethyl-4-methylanilino)adenine, HE-EMAA;
E) 9-(2-Hydroxyethyl)-$N^2$-(3,4-dichlorobenzyl)guanine, HE-DCBG;
F) 9-(2-Hydroxyethyl)-2-(3,4-dichlorobenzylamino)adenine, HE-DCBA;
G) 9-(4-Hydroxybutyl)-$N^2$-(3,4-dichlorobenzyl)guanine, HB-DCBG;
H) 9-(4-Hydroxybutyl)-2-(3,4-dichlorobenzylamino)adenine, HB-DCBA;
I) 9-(2-Carboxyethyl)-2-(3,4-dichlorobenzyl)guanine, CE-DCBG; and
J) 9-(2-Aminoethyl)-2-(3,4-dichlorobenzyl)guanine, AE-DCBG.

The compounds of the invention have utility in the treatment of mycoplasma and Gram-positive infections, and have special advantages in the treatment of organisms that have become resistant to currently used therapeutics. They may also be useful in basic identification of organisms which cause infections. The minimal inhibitory concentration (MIC) of 50 μM or less is desirable for a clinically relevant antibacterial or mycoplasma agent. The MIC may be determined using standard assays and the desirable level of inhibition is as noted above.

The organisms most likely to be treated by the methods of the invention are naturally occurring mycoplasma and Gram-positive bacteria which parasitize humans, livestock or commercially important animals including, but not limited to, pigs, cows, goats, chickens, turkeys, sheep, and laboratory animals (e.g., rats, mice, rabbits). Mycoplasmata and other bacteria which are the targets of the methods of the invention also include those mycoplasmata, etc., which opportunistically infect laboratory or other cultures of eukaryotic (e.g., plant, animal, and insect) cells.

The compounds may be administered both prophylactically and after infection has occurred. Prophylaxis may be most appropriate for immunocompromised animals and human patients and for animals and patients following surgery or dental procedures. This list of relevant conditions for application of the methods of the invention is not intended to be limiting, and any appropriate infection responsive to the compounds may be treated using the methods and/or compounds of the invention.

DETAILED DESCRIPTION

The Gram-positive Pathogens. There are three principle Gram-positive organisms which are amenable to treatment using the new compounds of the invention. Two of these *Staphylococcus aureus* and *Enterococcus fecalis/fecium*, are primarily nosocomial (hospital-acquired) pathogens; together, they presently account for the majority of nosocomial diseases. The third organism is the community-acquired pathogen, *Streptococcus pneumoniae*.

*Staphylococcus aureus* currently is the most frequent cause of nosocomial bacteremia and skin/wound infection and the second most frequent cause of nosocomial lower respiratory infection. *Enterococcus fecalis/fecium* ranks third behind *Staphylococcus aureus* and *Escherichia coli* as the cause of nosocomial septicemia, endocarditis, and infections of wounds and the urinary tract. *Streptococcus pneumoniae* causes several serious and potentially life-threatening diseases. In the United States it is estimated that *Streptococcus pneumoniae* accounts annually for 6,000 cases of pneumococcal meningitis, a half million cases of pneumonia, 55,000 cases of bacteremia, and 6 million cases of otitis media. Annual mortality from *Streptococcus pneumoniae*-induced disease is estimated to be 40,000 in the United States and 3–5 million globally.

There presently is a rapidly growing global crisis in the clinical management of life-threatening infectious disease caused by multi-antibiotic-resistant strains of the Gram-positive pathogens Streptococcus, enterococcus, and Staphylococcus. New Gram-positive specific antibiotic targets which can selectively hit these targets must be researched and developed as part of the effort to successfully meet this crisis. Provided herein is a novel class of pol III-selective xenobiotics which have clinical use.

Mycoplasmal Pathogens

Using *Mycoplasma pulmonis* as a model system, we have investigated whether the growth of mycoplasmata are sensitive to Gram-positive selective inhibitors of the HPUra-type.

6-(p-Hydroxyphenylazo)-uracil (HPUra) and a wide variety of structurally related derivatives (all deoxyribo-nucleotide analogs) are highly selective inhibitors of the replication of Gram-positive bacteria. Their site of action is replicative DNA synthesis, and their specific target within this site is Pol III. These properties of HPUra and its derivatives make them convenient and powerful probes with which to provisionally identify organisms that use Pol III as their replicative polymerase, and offer a previously unknown method to treat mycoplasmal infections.

Based upon our finding that HPUra derivatives inhibit mycoplasma, we propose that Mycoplasma has at least two distinct DNA polymerases; one is the Pol III enzyme. Presumably, all mycoplasmata have a Pol III enzyme. The second class of DNA polymerase in Mycoplasma is the ~100 kDa enzyme. Accordingly, previous suggestions that genome reduction during mycoplasmal evolution has resulted in the elimination of all but one DNA polymerase would seem to be incorrect.

Figure 1:
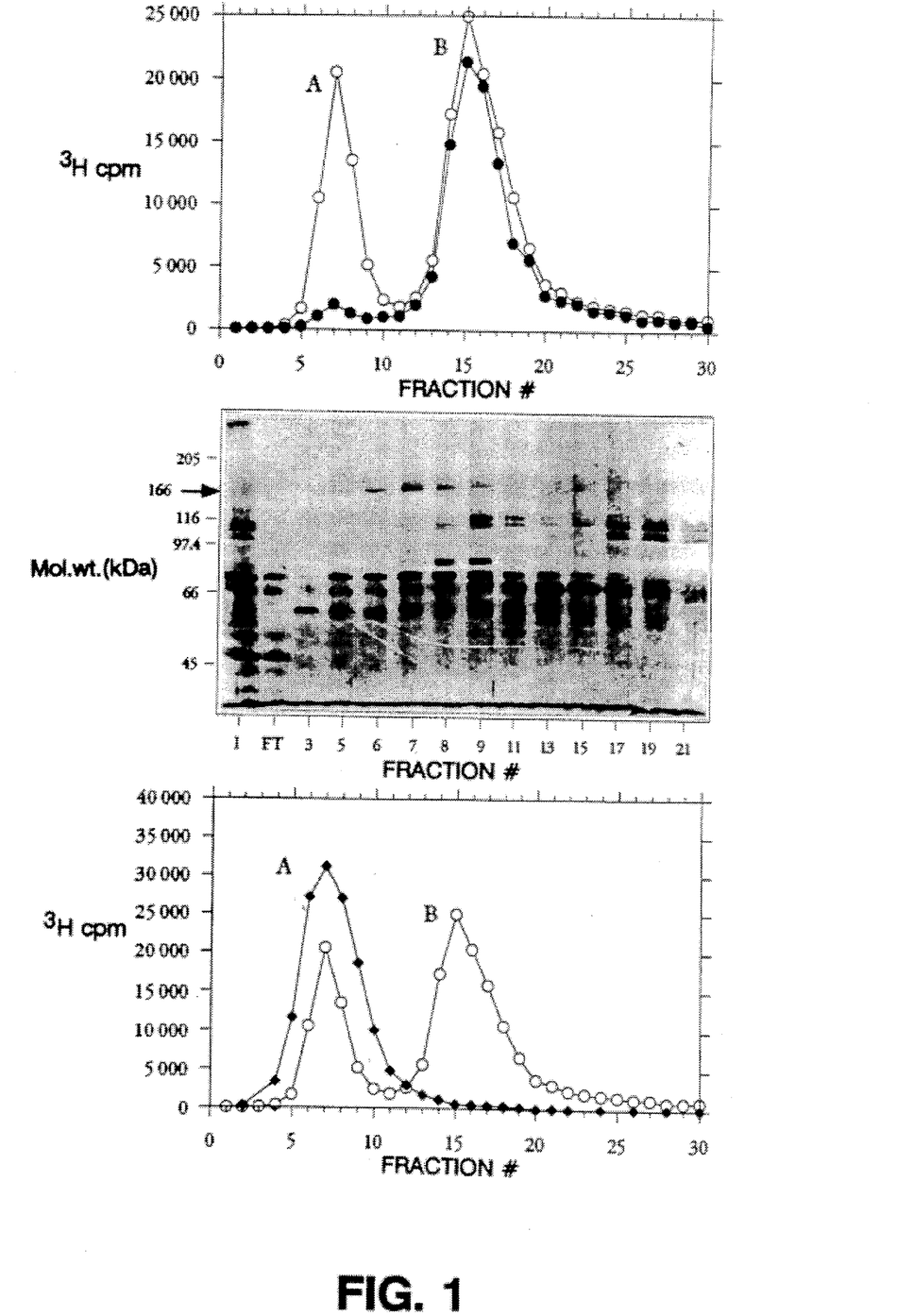
FIG. 1 is a graph showing analysis of the products of purification step V (Bio-Rex 70 chromatography). Top panel, pol activity in the presence (●) and absence (○) of 200 μM HPURa. The $^3$H cpm represent the level of polymerase activity present in 5 μl of the indicated fraction. Center panel, SDS-PAGE analysis; 25 μl of the column input (i) flowthrough (FT), and 25 μl from the indicated fractions (3–21) were denatured and electrophoresed. The gel was stained with Coomassie brilliant blue, destained, and dried to generate the electrophorogram shown. Bottom panel, display of exo (♦) vs. pol (○) activity; 5 μl of each fraction was assayed.

Presumably, the newly discovered *M. pulmonis* Pol III is the main DNA "replicase" of *M. pulmonis*. The highly developed functional specialization of the Gram-positive Pol III and the central importance of the enzyme to cell survival seem to have preserved its replicative function during mycoplasmal evolution. Its size and antigenicity (~166 kDa; FIG. 1) is similar to a typical Gram-positive Pol III. The conservation of replicative function is also indicated by the high level of sensitivity of mycoplasmal cell growth and division to the HPUra class of inhibitors. If *M. pulmonis* Pol III were not essential to DNA replication, it is very unlikely that its host would retain significant sensitivity to an inhibitor with the strict degree of Pol III specificity for which HPUra and its derivatives are noted (Brown, 1970, supra). Compounds which may be used to inhibit Mycoplasma A variety of compounds have been described which affect Gram-positive DNA polymerases. Generally, these compounds function as deoxyribonucleotide analog inhibitors and substrates of DNA polymerases. Examples of such compounds which may be used to inhibit replication of Gram-positive bacteria and mycoplasmata are pyrimidine or purine derivatives, 2-substituted dATP and $N^2$-substituted dGTP analogs, ribo-, 2'-deoxyribo-, arabino-, 2',3'-dideoxy- or acyclo-nucleotides, $N^6$-substituted 6-aminopyrimidines and $N^2$-substituted 2-aminopurines. For characterization of these compounds, see e.g., Wright and Brown, (1990) *Pharmac. Ther.* 47:447–497 (hereby incorporated by reference).

Extensive structure-activity relationship studies have revealed that the 3-position is the only position of the uracil ring that can be substituted without drastic reduction in pol III inhibitory potency (Brown and Wright, Pharmacology Therapy 47:447 (1990)). Substituents at this position can actually enhance inhibitor affinity for the polymerase target. For example, 3-alkyl TMAU derivatives (alkyl=Me. Et, n-Pr, n-Bu) are slightly more potent pol III inhibitors than the parent compound (Trantolo et al., Journal of Medical Chemistry). Third, as shown in the following table, these alkyl N3 substituents also can increase the antimicrobial potency of TMAU for relevant Gr+ organisms, especially antibiotic-resistant strains.

The 3-substituted uracils and isocytosines of the invention are of the general formulae:

Uracils    Isocytosines where $R_1$ in both uracils and isocytosines is $(CH_2)_nOH$, $CH_2CHOHCH_2OH$, $CH_2CHOHCH_3$, $(CH_2)_mCO_2H$, or $(CH_2)_nNH_2$, n is 2, 3, 4, or 5 and m is 1, 2, 3, or 4; and $R_2$ is where $R_3$ and $R_4$ are H, alkyl, halo, or any other hydrophobic constituents (e.g., $CH_3$, $C_2H_5$, F, Cl, Br, and $(CH_2)_3$).

Preferred 3-substituted uracil and isocytosine compounds are:

A) 3-(2-Hydroxyethyl)-6-(5-indanylamino)uracil, HE-TMAU;
B) 3-(2-Hydroxyethyl)-6-(5-indanylamino)isocytosine, HE-TMAiC;
C) 3-(2-Hydroxyethyl)-6-(3-ethyl -4-methylanilino)uracil, HE-EMAU;
D) 3-(2-Hydroxyethyl)-6-(3-ethyl-4-methylanilino)isocytosine, HE-EMAiC;
E) 3-(2-Hydroxyethyl)-6-(3,4-dichlorobenzylamino)uracil, HE-DCAU;
F) 3-(2-Hydroxyethyl)-6-(3,4-dichlorobenzylamino)isocytosine, HE-DCAiC;

Structure-Activity Relationship for N3-Alkyl TMAUS vs. Growth of *Staphylococcus aureus* and *B. subtilis*

| | Minimal Inhibitory Concentration (uG/ml) | | |
|---|---|---|---|
| X— = | Control SA | Methicillin-Resistant SA | Wild-Type BS |
| H— | 8 | 4 | 23 |
| $CH_3$— | Not Determined (ND) | ND | 7 |
| $C_2H_5$— | 1 | 0.5 | 4 |
| $nC_3H_7$— | ND | ND | 3.5 |
| $nC_4H_9$— | >>128 | 0.5 | 1.8 |
| Methicillin | 1 | 128 | ND |

Novel Compounds Useful to Inhibit DNA Pol III

Several novel compounds are useful as antibiotics in vivo and in vitro for the prophylaxis, inhibition, or eradication of pathogenic mycoplasmata. These compounds are primarily 3-substituted uracils and isocytosines, and 9-substituted guanines and adenines.

G) 3-(4-Hydroxybutyl)-6-(5-indanylamino)uracil, HB-TMAU;
H) 3-(4-Hydroxybutyl)-6-(5- indanylamino)isocytosine, HB-TMAiC;
I) 3-(Carboxymethyl)-6-(5-indanylamino)uracil, CM-TMAU; and
J) 3-(Aminoethyl)6-(5-indanylamino)uracil, AE-TMAU.

The 9-substituted guanines and adenines of the invention are of the formulae:

Guanines          Adenines where $R_1$ in both guanines and adenines is $(CH_2)_nOH$, $CH_2CHOHCH_2OH$, $CH_2CHOHCH_3$, $(CH_2)_mCO_2H$, or $(CH_2)_nNH_2$, n is 2, 3 4, or 5 and m is 1, 2, 3, or 4; and $R_2$ is where $R_3$ and $R_4$ are H, alkyl, halo, or any other hydrophobic constituents, e.g., $CH_3$, $C_5H_5$, F, Cl, Br, and $(CH_2)_3$.

Preferred 9-substituted guanine and adenine compounds are:
A) 9-(2-Hydroxyethyl)-$N^2$-(5-indanyl)guanine, HE-TMPG;
B) 9-(2-Hydroxyethyl)-2-(5-indanylamino)adenine, HE-TMAA;
C) 9-(2-Hydroxyethyl)-$N^2$-(3-ethyl-4-methylphenyl)guanine, HE-EMPG;
D) 9-(2-Hydroxyethyl)-2-(3-ethyl-4-methylanilino)adenine, HE-EMAA;
E) 9-(2-Hydroxyethyl)-$N^2$-(3,4-dichlorobenzyl)guanine, HE-DCBG;
F) 9-(2-Hydroxyethyl)-2-(3,4-dichlorobenzylamino)adenine, HE-DCBA;
G) 9-(4-Hydroxybutyl)-$N^2$-(3,4-dichlorobenzyl)guanine, HB-DCBG;
H) 9-(4-Hydroxybutyl)-2-(3,4-dichlorobenzylamino)adenine, HB-DCBA;
I) 9-(2-Carboxyethyl)-2-(3,4-dichlorobenzyl)guanine, CE-DCBG; and
J) 9-(2-Aminoethyl)-2-(3,4-dichlorobenzyl)guanine, AE-DCBG.

Therapeutic Administration of Compounds

The compounds herein before described are useful for the treatment of bacterial infections in humans caused by Gram positive bacteria, including strains resistant to common antibiotic drugs. The compounds are also useful for treatment of mycoplasma infections in humans caused by various species of the genera Mycoplasma and Ureaplasma. They are also useful for treatment of related Gram-positive bacterial infections and mycoplasmata infections in animals, and for eliminating or avoiding mycoplasmal infections of eukaryotic cell cultures.

The compounds of the invention can be formulated for pharmaceutical, veterinary, and tissue culture use, optionally together with an acceptable diluent, carrier or excipient and/or in unit dosage form. In using the compounds of the invention, conventional pharmaceutical, veterinary, or culture practice may be employed to provide suitable formulations or compositions.

Thus, for human or animal use, the formulations of this invention can be administered by parenteral administration, for example, intravenous, subcutaneous, intramuscular, intraorbital, ophthalmic, intraventricular, intracranial, intracapsular, intraspinal, intracisternal, intraperitoneal, topical, intranasal, aerosol, scarification, and also oral, buccal, rectal, vaginal, or topical administration.

The formulations of this invention may also be administered by the use of surgical implants which release the compounds of the invention.

Parenteral formulations may be in the form of liquid solutions or suspensions; for oral administration, formulations may be in the form of tablets or capsules; and for intranasal formulations, in the form of powders, nasal drops, or aerosols.

Methods well known in the art for making formulations can be found in, for example, "Remington's Pharmaceutical Sciences." Formulations for parenteral administration may, for example, contain as excipients sterile water or saline, polyalkylene glycols such as polyethylene glycol, oils of vegetable origin, or hydrogenated naphthalenes, biocompatible, biodegradable lactide polymer, or polyoxyethylene-polyoxypropylene copolymers may be used to control the release of the present factors. Other potentially useful parenteral delivery systems for the factors include ethylene-vinyl acetate copolymer particles, osmotic pumps, implantable infusion systems, and liposomes. Formulations for inhalation may contain as excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally. Formulations for parenteral administration may also include glycocholate for buccal administration, methoxysalicylate for rectal administration, or citric acid for vaginal administration.

The concentration of the compound in the formulations of the invention will vary depending upon a number of factors, including the dosage to be administered, and the route of administration.

In general terms, the compounds of the invention may be provided in an aqueous physiological buffer solution containing about 0.1 to 10% w/v compound for parenteral administration. General dose ranges are from about 0.01 mg/kg to about 1 g/kg of body weight per day; a preferred dose range is from about 0.01 mg/kg to 100 mg/kg of body weight per day. The preferred dosage to be administered is likely to depend upon the type and extent of progression of the infection being addressed, the overall health of the patient, and the route of administration. For topical and oral administration, formulations and dosages can be similar to those used for other antibiotic drugs, e.g., erythromycin.

Detection of Mycoplasma Infection and Evaluation of Efficacy/Toxicity of Compounds Detection of Infection Many standard methods of detecting mycoplasmata infection exist and may be used for both in vitro and in vivo use. The examples provided here are not intended to be limiting. Detection of Gram-positive bacterial infection may be carried out by any standard method (e.g., Gram staining).

A preferred method to detect mycoplasmal infection both in vitro and in vivo is the use of the polymerase chain reaction (PCR). This method can be used for both qualitative and quantitative evaluation of infection. Primers are selected from unique regions of the genome which are not conserved between Mycoplasma and Gram-positive bacteria, and reaction conditions are determined as is standard in the art (see e.g., Ochman et al. in *PCR Protocols: A Guide to Methods and Applications*, Academic Press: San Diego (1990). The presence of an amplified cDNA of the correct size is indicative of mycoplasmal infection. The cDNA may be sequenced for verification of mycoplasmal identity. Such primers are also useful for quantitative PCR (e.g., to determine efficacy of a compound to inhibit mycoplasma replication) using fewer amplification cycles. Appropriate protocols may be found in Ochman et al., supra. Samples for amplification may be obtained from cell cultures, or tissue or blood samples from animals or humans.

Evaluation of Efficacy of Antibiotic Compounds

The mycoplasmal inhibiting properties of novel and previously known compounds useful in the methods of the invention may be tested using the simple assay described in the Experimental Procedures below. Briefly, using standard mycoplasmal growth conditions on agar plates with or without supplementation by test compounds, growth inhibition at various concentrations can be evaluated for any test compound. Alternatively, the test compound may be applied to liquid cultures at varying concentrations and growth inhibition monitored. Growth inhibition, i.e. of cell replication, by plate, a MIC of 50 µm or less; in liquid medium, inhibition of 90% at 100 µm or less.

A direct method to assay for a test compound's ability to inhibit the activity of DNA Pol III is by using a DNA polymerase assay as described (Barnes and Brown *Nuc. Acids Res.*, 6:1203–19 (1979); Trantolo et al. (1986) *J. Med. Chem.* 29:676–681;Mills et al., *J. Bacteriol.*, 132:641–49 (1977); and Low et al., *J. Biol. Chem,*, 251:1311–25 (1976); all hereby incorporated by reference). This rapid screening method can use natural or recombinant DNA pol III enzyme in a standard DNA polymerase activity assay. There are numerous methods for such assays known in the art (see above references, for example). By including a test compound in a side-by-side assay with a control, the effect of the test compound on polymerase activity can be assessed. Test compounds with an appropriate level of inhibition of the natural or recombinant mycoplasmal DNA polymerase III are good candidate therapeutics for further evaluation.

Evaluation of Toxicity

Toxicity of the novel compounds described above will be evaluated according to standard methods known to those skilled in that art (see Gootz, T. D. (1990) Clin. Microbiol. Rev., 3, 13–31). Determination of the toxic dose (or "$LD_{50}$") can be carried out as described in the Experimental procedures or using other protocols well known in the field of pharmacology, and a suitable range of $IC_{50}$ values for a compound to considered for further therapeutic evaluation will be on the order of the MIC or $IC_{50}$ in cultures, i.e., the therapeutic index should be greater than 10.

Experimental procedures

Mycoplasmal growth and drug inhibition

*M. pulmonis* strain KD735-15 (construction described in Bhugra and Dybvig, 1992) was propagated in mycoplasmal medium, and colony-forming units (cfu) were assessed on agar as previously described (Dybvig and Cassell, 1987). *M pulmonis* is a representative species which is well characterized. Other publicly available strains may also be used. For example, *Mycoplasma agalactiae*, ATCC 35890, *Mycoplasma arthritidis* ATCC 13988, *Mycoplasma bovigenitalium*, ATCC 14173, *Mycoplasma bovirhinis, ATCC* 27748, *Mycoplasma bovis*, ATCC 25025, *Mycoplasma felis*, ATCC 23391, *Mycoplasma gallinaceum*, ATCC 33550, *Mycoplasma gallinarum*, ATCC 15319, *Mycoplasma gallisepticum*, ATCC 15302, *Mycoplasma genitalium*, ATCC 33530, *Mycoplasma hominis*, ATCC 14027, *Mycoplasma hyorhinis*, *ATCC* 17981, *Mycoplasma hyosynoviae*, ATCC 25591, *Mycoplasma meleagridis*, ATCC 25294, *Mycoplasma orale*, ATCC 15539, *Mycoplasma pneumoniae*, ATCC 15293, *Mycoplasma pullorum, ATCC* 33553, *Mycoplasma pulmonis*, ATCC 14267, *Mycoplasma putrefaciens*, ATCC 15718, *Mycoplasma synoviae*, ATCC 25204, may also be used. The inhibitors used here were prepared as described in Wright and Brown ((1990) *Pharmac. Ther.* 47:447–497) and were prepared at a stock concentration of 20 mM in dimethyl sulphoxide (DMSO). Growth inhibition was examined on agar by comparing cfu obtained on medium lacking or supplemented with antibiotic. DMSO alone at concentrations as high as 1% had no effect on growth or cfu capacity of *M. pulmonis*.

Enzyme purification

General methods for purification and identification of DNA polymerase III from gram-positive bacteria are known in the art. Provided here is the protocol for isolation of a 5 L culture of *M. pulmonis* was grown to mid-log phase and rapidly cooled to 4° C. The cells were harvested by centrifugation at 4° C. and washed twice by recentrifugation from ice-cold, phosphate-buffered saline (150 mM BaCl:10 mM potassium phosphate, pH 7.6). The packed cells (~3.5 g) were rapidly frozen as 0.7 g pellets in a dry ice-ethanol bath and stored at −80° C. The following procedure, summarized in Table 1, applies to the purification of a single 0.7 g pellet.

Fraction I (Crude extract): All procedures were carried out at 4° C., and the protein concentration of fractions was determined by the method of Bradford (*Anal. Biochem.*, 72:248–54 (1976)), using a bovine serum albumin standard. A single cell pellet was resuspended in 1 ml of column buffer (50 mM potassium phosphate, pH 7.5; 1 mM PMSF). The cells were disrupted in a French pressure cell at approximately 138,000 kPa and centrifuged at 20,000×g for 60 min to generate a clear supernatant (Fraction I).

Fraction II (ammonium sulphate precipitation): Fraction I was mixed with three volumes of a saturated solution of ammonium sulphate in 50 mM Tris-HCl (pH 8.0):2 mMDTT. The resulting cloudy suspension was stirred for 1 h and centrifuged at 20,000×g for 20 min. The pellet was dissolved in 3 ml of column buffer containing 1.5M NaCl, and the resultant solution was clarified by centrifugation to yield Fraction II.

Fraction III (phenyl sepharose eluate): Fraction II was applied to a 1 ml phenyl sepharose (Sigma Chemical Corp.) column equilibrated in column buffer containing 1.5M NaCl. The column was washed with 2 vol. of the same buffer and subsequently with 1.1 vol. of column buffer. The column was eluted with 3 vol. of column buffer containing 1% Triton X-100 to generate Fraction III.

Fraction IV (macro-prep high econo Q chromatography): Fraction III was applied to a 2 ml column of macro-prep high-capacity econo Q (Bio-Rad) equilibrated with column buffer containing 1% Triton X-100. The column was then washed with approximately 10 ml of the same buffer, and eluted with a 40 ml gradient of 0–0.2M NaCl (also based in the same buffer). A broad peak of DNA polymerase activity eluted at approximately 0.08M NaCl, and the active fractions were pooled to generate Fraction IV.

Fraction Va (Bio-Rex 70 chromatography): Fraction IV was diluted with column buffer containing 1% Triton X-100 to reduce the concentration of NaCl to 25 mM, and then applied to a 2 ml Bio-Rex 70 (Bio-Rad) column equilibrated in column buffer containing 1% Triton X-100+25 mM NaCl. The column was washed with 5 ml of the same buffer, and the adsorbed enzyme was eluted in two distinct peaks (designated A and B) at approximately 0.15 and 0.30M NaCl, respectively. The chromatogram is summarized in FIG. 1. As the top panel of the figure indicates, peak A represents the HPUra-sensitive pol activity. Peak A was pooled to generate Fraction Va.

Enzyme assays and determination of inhibitor $IC_{50}$ values

DNA pol activity was assayed as described (Barnes et al., NuC. Acids Res., 6:1203–19 (1979)), using activated calf-thymus DNA as template primer, 10 pM [$^3$H-methyl]-dTTP as the labelled dNTP substrate, and dATP, dCTP, and dGTP at 25 µM each. For determination of $IC_{50}$ values of TMAU and the four arylazopyrimidines (summarized in Table 2), the concentration of dGTP was reduced from 25 to 10 µM. TMAU was used directly in enzyme assays, and arylazopyrimidines were reduced prior to assay to the active, hydrazino forms, using sodium dithionite as described by Wright and Brown (1977) J. Med. Chem. 20:1181–1185.

Exo activity was assayed as described by Low et al. (1976), supra, using denatured calf-thymus DNA incorporating [$^3$H]-dTMP residues at the 3'-OH ends.

SDS-PAGE and immunoblot analysis of Bio-Rex fractions

SDS-PAGE exploited the method of Laemmli (1970) and employed 1.5 mm×83 mm×102 mm, 15-well gels containing 7.5% polyacrylamide (Bio-Rad) and 0.2% bis-acrylamide (Bio-Rad). For immunoblot analysis, 25 µl samples of selected Bio-Rex chromatographic fractions or other control fractions of interest were denatured (Laemmli, 1970) and subjected to SDS-PAGE. Gels were blotted to nylon-reinforced nitrocellulose membranes (Nitro Plus 2000,Micron Separations, Inc.) and subjected to the following immunoblot analysis based on the method of Towbin et al., Proc. Natl. Acad. Sci. USA, 76:4350–54 (1979). The blots were exposed to primary antibody (rabbit polyclonal anti-Pol III IgG; (Barnes et al., (1979) supra) at a concentration of 2.5 µg ml$^{-1}$. The secondary antibody (biotinylated goat anti-rabbit IgG; Sigma) was used at a concentration of 5 µg ml$^{-1}$. Following treatment with the second antibody the blots were stained with streptavidin-linked horseradish peroxidase (Sigma; 5 µg ml$^{-1}$), rinsed, and developed with $H_2O_2$/o-dianisidine.

The following examples are intended to illustrate the invention and are not intended to be limiting

EXAMPLES

Example 1

Inhibition of mycoplasmal growth with antimicrobials of the HPUra Type

HPUra and 25 other agents selected from a large collection of structurally related compounds (Wright and Brown, 1990, Pharmac. Ther. 47:447–497) were tested against M. pulmonis at a concentration of 200 µM as described in the Experimental procedures. HPUra and 15 others completely inhibited colony formation. Of these, HPUra and three others (6-(phenylazo)uracil (PUra), 6-(p-chlorophenylazo) uracil (PCPUra), and 6-(m-chlorophenylazo)uracil (MCPUra)) were compared with respect to potency in a series of decreasing concentrations (100, 50, 25, 12.5 and 6.25 µM). The concentration of each agent that was required to inhibit colony formation by 99% was as follows: PCPUra<6.25 µM; PUra, 6.25–12.5 µM; MCPUra, 12.5 µM; and HPUra, 12.5–2.5 µM. Thus these agents displayed a level of potency against M. pulmonis that was fully equivalent to that displayed against low-GC Gram-positive bacteria such as B. subtilis, Enterococcus faccalis, and Staphylococcus aureus (Barnes et al., (1979) supra).

Example 2

Isolation of a DNA polymerase activity from M. pulmonis similar to that of a Gram-positive Pol III The sensitivity of the growth of M. pulmonis to HPUra and its close derivatives indicated that the organism carried an appropriate enzyme target. To explore this suggestion, we prepared a crude extract of M. pulmonis (Fraction 1 as defined in the Experimental procedures) and examined it for the presence of a polymerase activity which was sensitive to HPUra and similar agents. The extract displayed a level of pol activity that would be expected for a low-GC Gram-positive organism, and a significant portion of this activity (~50%) was HPUra sensitive (results not shown).

To characterize the HPUra-sensitive pol activity further, we purified it using a five-step scheme summarized in Table 1 and described in the Experimental procedures. FIG. 1 summarizes an analysis of the Bio-Rex 70 chromatogram of pol activity developed in step V, the final step of the procedure. As the activity curve (open circle symbols) of the top panel indicates, Bio-Rex chromatography resolved two peaks of pol activity, A and B. Re-assay of the fractions in the presence of 200 µM HPUra (filled circle symbols) indicated that the pol activity represented by peak A was drug-sensitive, while that of peak B was insensitive.

TABLE 1

Summary of Pol III Purification

| FRACTION | UNITS[1] | mg PROTEIN | SPECIFIC ACTIVITY (UNITS mg$^{-1}$) |
|---|---|---|---|
| I. Crude extract | 7.8 | 28 | 0.28 |
| II. Ammonium sulpahte ppt. | 30.9[2] | 25 | 1.2 |
| III. Phenyl sepharose | 37.5 | 7.2 | 5.2 |
| IV. Econo Q | 25.7 | 0.83 | 31 |
| V. Bio-Rex 70 | 7.4 | 0.11 | 65 |

[1]One unit is equal to the amount of TMAU-sensitive enzyme required to catalyze the incorporation of 1 nmole [$^3$H]-dTMP into acid-precipitable material in 10 min under the assay conditions.
[2]The apparent increase in the activity at this step results from the removal of an inhibitory substance.

To determine if the pol activity in peak A was similar to a Gram-positive-specific Pol III, we evaluated whether a) the activity display the appropriate level of sensitivity as representative Gram-positive Pol III-specific inhibitors; b) the activity was associated with a polypeptide of a similar size (i.e., ~160 kDa); and c) the activity was associated physically with an exo activity. The results of these inquiries are described below.

a) Sensitivity of peak A pol activity to HPUra-type inhibitors

Five compounds were used to assess the sensitivity of peak A pol activity to HPUra-type inhibitors. These were the four compounds used in the growth experiment described above (HPUra, PUra, PCPUra, and MCPUra) as well as TMAU (6-(3',4'-trimethylanilino) uracil), a 'second generation' derivative of the HPUra prototype, equivalent in mechanism and target specificity (Wright and Brown, 1990). The $IC_{50}$ value (the concentration required for 50% inhibition) of each of these agents was determined for the peak A pol activity and for an inhibitor-sensitive control enzyme, B. subtilis Pol III. The results, summarized in Table 2, indicated that the peak A polymerase typified a Gram-positive-specific Pol III with respect to inhibitor sensitivity.

TABLE 1

Inhibitor Sensitivity of *B. subtilis* and *M. pulmonis* DNA polymerases

| | $IC_{50}$[3] | |
|---|---|---|
| | *B. subtilis*[4] | *M. pulmonis*[5] |
| HPUra | 11 | 14 |
| PUra | 34 | 20 |
| MCPUra | 48 | 17 |
| PCPUra | 57 | 31 |
| TMAU | 8 | 11 |

[3]Concentration (µM) required for 50% inhibition of polymerase activity; assay conditions are defined in the Experimental procedures.
[4]*B. subtilis* Pol III was prepared and used as described by (Barnes et al., (1979) supra).
[5]Fraction 7 from peak A, Bio-Rex 70 chromatogram of FIG. 1.

b) Identification of a ~166 kDa polypeptide associated with peak A pol activity

SDS-PAGE was used to examine whether a Pol III-specific polypeptide of ~160 kDa was associated with peak A. The middle panel of FIG. 1 displays the SDS-PAGE analysis of samples of relevant fractions of the chromatogram shown in the top panel. It indicates the coincidental elution, in fractions 6–9, of the catalytic activities of peak A and a polypeptide of ~166 kDa (noted by an arrow on the y-axis), the size expected for a typical Gram-positive-specific Pol III.

To determine if the latter peptide was, in fact, Pol III, we subjected the peak fraction (no. 7) of peak A and, as a control, the peak fraction (no. 15) of peak B to SDS-PAGE/immunoblot analysis. The analysis exploited a polyclonal antibody raised against the 162.4 kDa *B. subtilis* Pol III. This reagent reacts strongly and specifically not only with blotted *B. subtilis* Pol III, but also with those of several other Gram-positive organisms such as Staphylococcus and Streptococcus (Barnes et al., (1979) supra). The results of the analysis, which are not shown, clearly indicated that the ~166 kDa polypeptide band of peak A was strongly reactive for the antibody and was the only gel band of either peak that specifically reacted with the antibody probe.

c) Physical association of the peak A pol activity with exo activity

The fractions of the chromatogram shown in the top panel of FIG. 1 were analyzed for exo activity. These results and those of the previous pol assay were plotted to generate the composite activity profile of the lower panel of FIG. 1. The profile indicates a single sharp peak of exo activity (filled diamond symbols) perfectly coincident with the peak of HPUra-sensitive pol activity (open circle symbols; peak A). Although the pol-exo coincidence was consistent with what would be expected for a typical Gram-positive-specific Pol III polypeptide, it was nevertheless possible that the exo activity was associated with an unrelated protein which fortuitously co-chromatographed with the HPUra-sensitive pol activity.

To determine if the pol-exo functions were separate or physically associated, we took advantage of two basic properties of the mechanism of interaction of Gram-positive Pol IIIs and agents of the HPUra class. One is the inherent inhibitor resistance of its exo activity in the presence of a single-stranded (ss) DNA substrate, and the other is the physical sequestration of enzyme which forms the basis of agent-induced pol inhibition in the presence of double-stranded (ds) DNA. These two properties and the experiment that exploited them are explained briefly below.

Sequestration:

Although formally pyrimidines, inhibitors of the HPUra class incorporate a novel base-pairing domain which endows them with the capacity to specifically mimic the purine dNTP, dGTP, and compete with its binding to template cytosine. The capacity of these agents to inhibit the pol activity of their target—a capacity which can be specifically and competitively antagonized by dGTP—is strictly dependent on the provision of a specific primer-template structure in the pol reaction. The template must be H-bonded to a 3'-OH-terminated primer, and must contain the inhibitor complement, cytosine, and present it as the first unpaired residue proximal to the primer terminus. When provided with this dsDNA structure, the inhibitor inserts its aryl substituent into the enzyme's dNTP-binding site and simultaneously forms three H bonds with the unopposed template cytosine. As a result, the enzyme becomes firmly sequestered to the DNA in a catalytically inactive, protein-inhibitor-template primer complex. As expected, dGTP specifically competes with the inhibitor to antagonize the formation of this complex.

Inhibitor-resistant exo activity on ssDNA:

Because the Gram-positive-specific Pol III is a primer-driven enzyme, its pol site cannot utilize ssDNA to catalyze dNTP polymerization. In contrast, the enzyme's exo site prefers ssDNA, binding and digesting it at least 100 times more efficiently than dsDNA. If a polymerase molecule is exposed to an HPUra-type inhibitor while its exo site is digesting ssDNA, essentially no inhibition is observed. However, when the same reaction is first supplemented with an appropriate ds template primer, it is strongly inhibited upon exposure to the drug. The basis for the sensitizing effect of the dsDNA is simply its capacity to foster inhibitor-induced enzyme sequestration, a process that physically entraps the enzyme protein and prevents its exo site from acting on ssDNA. As expected from consideration of mechanism, dGTP specifically antagonizes this sequestration-induced inhibition.

Example 3

Effects of HPUra and structurally related compounds on activity

Preliminary experiments, the results of which are not shown, indicated that the activity of the peak A exo on ssDNA was resistant to TMAU at 50 µM, a concentration at least 50 times that of its 'pol' $K_1$ on *B. subtilis* Pol III (Wright and Brown, 1977). Given this result, we further examined whether the exo activity of the peak A enzyme on ssDNA becomes susceptible to TMAU-induced sequestration when the reaction is supplemented with double stranded primer template, and if so, if the susceptibility is selectively antagonized by dGTP, the specific competitor of inhibitor-induced sequestration.

The results of the experiment are summarized in Table 3. TMAU at 50 µM inhibited ssDNA digestion by about 70% in the presence of dsDNA. When the latter mixture was supplemented with 500 µM dGTP, the specific antagonist of TMAU-induced sequestration inhibition was reduced to a level of <3%. In contrast, the same concentration dATP, a 'control' dNTP without effect on TMAU-induced sequestration, had no significant effect on the level of inhibition. Together, these results indicated that the exo and pol activities are strongly associated in an inhibitor-sequestrable unit similar to a Gram-positive-specific Pol III.

TABLE 3

Sequestration of the exo activity of peak A pol by TMAU Addition

| TMAU (50 μM) | dATP (500 μM) | dGTP (500 μM) | Activity[6] (%) |
|---|---|---|---|
| − | − | − | 100 |
| − | + | − | 101 |
| − | − | + | 103 |
| + | − | − | 31 |
| + | + | − | 31 |
| + | − | + | 98 |

[6]Exo activity was assayed on 3'-([$^3$H]-thymidine)-labelled ssDNA under 'sequestering' conditions in the presence of dsDNA as described in the Experimental procedures 100% activity is equivalent to the release of ~6000 c.p.m. (of 16,000 acid-precipitable c.p.m. per assay).

Example 4

Organic Synthesis of Compounds of the Invention

The following is an example of a method of synthesis of 3-substituted uracil and isocytosine compounds. This example is not intended to be limiting.

Example 4a

Preferred compounds are HE-TMAU and HE-TMAiC. Synthesis follows generally the method in Nogimori et al., *J. Med. Chem.* (1985) 28:1692–1694.

Steps of Synthesis 6-(5-Indanylamino)-2-thiouracil (a). 6-Amino-2-thiouracil is heated for 4 hours at 160° C. with an equimolar mixture of 5-aminoindan and the hydrochloride of 5-aminoindan. The product is crystallized from ethanol/water and isolated in 6% yield, mp 269°–272° C.

2-Methylmercapto-6-(5-indanylamino)-4-pyrimidone (b). Compound a is dissolved in ethanolic potassium hydroxide, and the solution is treated with methyl iodide at rt. After stirring for one hour, the solution is evaporated and the residue crystallized from ethanol. The product is isolated in 89% yield, mp 235°–238° C.

1- and 3-(2-Acetoxyethyl)-2-methylmercapto-6-(5-indanylamino)-4-pyrimidones, (c and d). Compound b is dissolved in ethanolic potassium hydroxide and the solvent is evaporated. Dry N,N-dimethylformamide is added, and the solution is cooled to 4° C. 2-Acetoxyethyl bromide is added and the mixture is stirred at 4° C. for 3 days. Evaporation of the solvent and chromatography of the residue on silica gel separates compounds c and d in ca. 3:1 ratio. The isomers are identified by characteristic $^1$H NMR signals [Nogimori et al., 1985].

3-(2-Hydroxyethyl)-6-(5-indanylamino)uracil, HE-TMAU (e). Compound d is heated at reflux in a mixture of conc. hydrochloric acid and methanol for one hour. The residue after evaporation of solvents is crystallized from aqueous ethanol.

3-(2-Hydroxyethyl)-6-(5-indanylamino)isocytosine, HE-TMAiC (f). Compound d is heated in a sealed bomb with ammonia-saturated methanol at 120° C. for 2 hours. The residue after evaporation of solvent is crystallized from water.

Example 4b

The following is an example of a method of synthesis of 9-substituted guanine and adenine compounds. This example is not intended to be limiting.

Preferred compounds are HB-DCBG and HB-DCBA. Synthesis is as follows:

-continued

The general procedure for synthesizing 9-substituted guanines is as follows:

a) 2-Bromohypoxanthine and 34-dichlorobenzylamine are heated at reflux in 2-methoxyethanol as described (Wright and Dudycz, *J. Med. Chem.*, 27:175 (1984)). $N^2$-(3.4-Dicholorobenzyl) gnanise (DCBG) is obtained in 83% yield.

b) DCBG is heated with thionyl chloride in dimethylformanide for 1 h. Crystallization from emthanol gives 84% of 2-(34-dischlorabenzylamino)-6-chloroparine.

c) Sodium hydride (60% suspension in mineral oil) is added in an equimolar amount to a suspension of 2-(3,4-dischlorobenzylamino)- 6-chloropurine (0.35 g/100 ml) in anhydrous acetonitrile at room temperature (rt). After stirring for 1 hr, the appropriate 4-acetoxybutyl bromide (1 eq.) is added, and the suspension is stirred for 48 hrs at rt. An equal volume of chloroform is added, and after filtration through Celite, the filtrate is evaporated to dryness. The residue is chromatographed on silica gel (230–400 mesh) and the products are eluted with chloroform to give the major 2-(3,4-dichlorobenzyl-amino-6-chloro-9-(4-acetoxybutyl)purine and then the minor 7 isomer.

d) A suspension of the 9-isomer from above in 0.5N sodium hydroxide solution is heated at reflux for 2 hr. After neutralization with 0.5N hydrochloric acid, the solution is placed in the refrigerator overnight. The colorless solid is collected and crystallized from dimethylformacomide (HB-DCBG).

e) A mixture of the 9 isomer from step c) is heated in a sealed bomb with ammonia-saturated methanol at 120° C. for 5 hours. Crystallization of crude product from methanol affords HB-DCBA.

The examples provided above are meant to illustrate the synthesis and characterization of a representative subset of the compounds of the invention. Analogous methods known to one skilled in the art can be used for the synthesis and characterization of other compounds of the invention (see, "Advanced Organic Chemistry," J. Mar., 3rd. ed., New York: John Wiley, 1985; "The Chemistry of Functional Groups," S. Patai, Ed., New York: John Wiley, multiple volumes, 1960ff; Heterocyclic and nucleoside synthesis—"Purines," J. H. Lister, New York: Wiley-Interscience, 1971; "Chemistry of Nucleosides and Nucleotides," Vols 1 and 2, L. B. Townsend, Ed., New York: Plenum Press, 1988;Medicinal chemistry—"The Basis of Medicinal Chemistry," 4th ed., 3 vols., M. E. Wolff, Ed., New York: Wiley-Interscience, 1980, all incorporated herein by reference).

EXAMPLE 5

Detection of mycoplasma in vivo and in vitro

A protocol which is useful for identifying mycoplasmal infection in cultured cells or cells placed in primary culture from human or animals is a DNA labelling method, which may be conducted as follows.

In situ DNA fluorescence is a very efficient method of screening for mycoplasma contamination in cell cultures. Bisbenzimide (Hoechst 33258) and DAPI (4',6-Diamidino-2-phenylindole) are DNA fluorochromes which bind specifically to the Adenine-Thymidine (A-T) regions of DNA. Cultures contaminated with mycoplasma will have small, uniformly shaped fluorescent bodies evident in the extranuclear and intracellular spaces. Nuclei of cultured cells will also fluoresce.

Artifacts may fluoresce and interfere with interpretation. They will appear larger in size than mycoplasma and irregular in shape. Using healthy, log-phase indicator cells and test cells will reduce interference caused by artifacts.

Materials

Indicator cells, Vero (ATCC® CCL 81) or 3T6-Swiss albino (ATCC CCL 96)

Leighton tubes or glass cover slips/culture dishes

Cell culture medium (growth medium)

Methanol

Glacial acetic acid

Bisbenzimide or DAPI

Mounting Solution McIlvaine's Buffer: Glycerol [1:1]

Fluorescent microscope

Procedure

Culturing samples and indicator cells

1. Seed indicator cells at low density in a Leighton tube or on a glass coverslip in a culture dish containing tissue culture medium. Incubate for 24 hours at the conditions appropriate for the culture medium (typically 37° C. at 5% or 2% $CO_2$). Prepare enough cultures to inoculate with control and test samples.

2. To separate indicator cell cultures, add 0.1 ml of test samples. Negative control: Indicator cell cultures inoculated with 0.1 ml of culture medium. Positive control: If a positive control is desired, infect a culture of the indicator cells with 0.1 ml of a viable culture of mycoplasma species.

3. Allow all cultures to incubate for an additional 4 days. NOTE: It is important to stain and examine cultures before they reach confluency. Adjust incubation time and inoculum density according to the growth characteristics of the test and indicator cells.

Fixing Cells

1. Prepare Carnoy's fixative fresh on the day of use. Solution consists of 3 parts methanol to 1 part glacial acetic acid. Prepare enough solution to fix all cultures. Approximately 15 ml of fixative is required per culture.

2. Without decanting growth medium, add approximately 5 ml of Carnoy's fixative to each culture and allow to stand 2 minutes.

3. Decant and add 5 ml of fixative to the cultures and allow to stand 5 minutes.

4. Decant fixative, add 5 ml of fresh fixative, and allow to stand 5 minutes.

5. Finally, decant fixative and allow growth surface to air dry approximately 5 minutes.

Staining and Mounting Cells

1. Prepare working concentrations of fluorochrome stain (Bisbenzimide) by dissolving 0.25–0.5 mg/ml of distilled water. Concentration of stock solution should be mg/ml and stored in the dark. Stock solution should be sterile and discarded if performance deteriorates. Note: DAPI may be substituted for bisbenzimide. Solubilize DAPI in Phosphate Buffered Saline (PBS) at 0.1 mg/ml. Stain cells for 15–30 minutes.

2. Completely immerse the growth surface in the stain solution and allow to stand for 30 minutes.

3. Rinse twice with distilled water.

4. Mount growth surface, cell side down, with a drop of mounting solution on a microscope slide. Slides may be preserved by sealing the edges of the cover slip and slide with clear nail polish. Slides should be protected from light and heat. These will last several weeks without quenching if properly stored.

Examining Cultures

A fluorescent microscope capable of epifluorescence is needed for visualizing the stain preparations. A typical system includes fluorescent microscope with a 53/44 barrier filter and a BG-3 exciter filter. A total magnification of 500×(40×X; 12.5) is usually sufficient to visualize mycoplasma but higher magnification may be used. These methods are derived from (Chen, *Exp. Cell Res.*, 104:255–62 (1977); Hay et al., *Nature*, 339:387–88 (1989); and McGarity et al., *In: Methods in mycoplasmology, Tully and Razin (eds).*, 2:487–88 (1983).

Uses/Advantages of the Invention

The compounds of this invention are inhibitors of the DNA polymerase III enzymes from Gram-positive bacteria, specifically, pathogenic Enterococci, streptococci, staphylococci, and strains thereof resistant to currently used antibiotics and are also inhibitors including mycoplasmata of the genera Mycoplasma and Spiroplasma and Ureaplasma. Inhibition of DNA polymerase III, the enzyme responsible for replication of the genome of the organism, causes inhibition of growth of the organism. The derivatives contain hydroxyalkyl, aminoalkyl or carboxyalkyl groups that increase water solubility of the compounds, facilitating their absorption and distribution in humans and animals, without interfering with their inhibition of growth of gram positive bacteria and mycoplasma spp.

The compounds of the invention can be used as screening tools to provisionally identify the DNA replicase 'phenotype' of an organism and, beyond that, as refined genetic and physical probes with which to dissect the machinery of mycoplasma DNA metabolism.

The low toxicity of HPUra and its close derivatives in mammalian cells (Brown et al., 1986, supra) also endows this class of agents with the characteristics required of Gram-positive- and mycoplasma-specific therapeutic antimicrobials. For example, they may be applicable in the clinic as chemotherapeutic agents capable of circumventing the natural and acquired resistance of pathogenic mycoplasmata to conventional antimicrobials.

What is claimed is:

1. A 3-substituted uracil compound, or pharmaceutically acceptable salt thereof, having the formula wherein $R_1$ is $(CH_2)_nOH$, $CH_2CHOHCH_2OH$, $CH_2CHOHCH_3$, $(CH_2)_mCO_2H$, or $(CH_2)_nNH_2$, n is 2, 3, 4, or 5 and m is 1, 2, 3, or 4; and $R_2$ is a 5-indanyl, where $R_3$ and $R_4$ are H, alkyl, or halo.

2. The compound of claim 1 wherein the 3-substituted uracil is 3-(2-Hydroxyethyl)-6-(5-indanylamino)uracil (HE-TMAU).

3. The compound of claim 1 wherein the 3-substituted uracil is 3-(2-Hydroxyethyl)-6-(3-ethyl-4-methylanilino)uracil (HE-EMAU).

4. The compound of claim 1 wherein the 3substituted uracil is 3-(2-Hydroxyethyl)-6-(3,4-dichlorobenzylamino)uracil (HE-DCAU).

5. The compound of claim 1 wherein the 3-substituted uracil is 3-(4-Hydroxybutyl)-6-(5-indanylamino)uracil (HB-TMAU).

6. The compound of claim 1 wherein the 3-substituted uracil is 3-(Carboxymethyl)-6-(5-indanylamino)uracil (CM-TMAU).

7. The compound of claim 18 wherein the 3-substituted uracil is 3-(Aminoethyl)-6-(5-indanylamino)uracil (AE-TMAU).

8. A 3-substituted isocytosine compound, or pharmaceutically acceptable salt thereof, having the formula wherein $R_1$ is $(CH_2)_nOH$, $CH_2CHOHCH_2OH$, $CH_2CHOHCH_3$, $(CH_2)_mCO_2H$, or $(CH_2)_nNH_2$, n is 2, 3, 4, or 5 and m is 1, 2, 3, or 4; and $R_2$ is a 5-indanyl, where $R_3$ and $R_4$ are H, alkyl, or halo.

9. The compound of claim 8 wherein the 3-substituted isocytosine is 3-(2-Hydroxyethyl)-6-(5indanylamino)isocytosine (HE-TMAiC).

10. The compound of claim 8 wherein the 3-substituted isocytosine is 3-(2-Hydroxyethyl)-6-(3-ethyl-4methylanilino)isocytosine (HE-EMAiC).

11. The compound of claim 8 wherein the 3-substituted isocytosine is 3-(2-Hydroxyethyl)-6-(3,4dichlorobenzylamino)isocytosine (HE-DCAiC).

12. The compound of claim 8 wherein the 3-substituted isocytosine is 3-(4-Hydroxybutyl)-6-(5indanylamino)isocytosine (HB-TMAiC).

* * * * *

UNITED STATES PATENT AND TRADEMARK OFFICE
CERTIFICATE OF CORRECTION

PATENT NO. : 5,516,905

DATED : May 14, 1996

INVENTOR(S) : Brown et al.

It is certified that error appears in the above-identified patent and that said Letters Patent is hereby corrected as shown below:

Col. 5, line 67, "HPURa" should be --HPUra--.

Col. 9, line 25, "C$_5$H$_5$" should be --C$_2$H$_5$--.

Col. 15, line 1, "Table 1" should be --Table 2--.

Col. 19, line 20, "6%" should be --66%--.

Col. 23, line 27, insert --50-- before "mg/ml".

Col. 23, line 47, ".500 X(40xX; 12.5)" should be --500X (40X; 12.5)--.

Col. 24, line 52, "18 should be --1--.

Col. 26, line 2, after "4" insert --"-"--.

Col. 26, line 5, after "4" insert --"-"--.

Col. 26, line 8, after "5" insert --"-"--.

Signed and Sealed this

Fifteenth Day of July, 1997

Attest:

Attesting Officer

BRUCE LEHMAN

Commissioner of Patents and Trademarks